Figure 1:
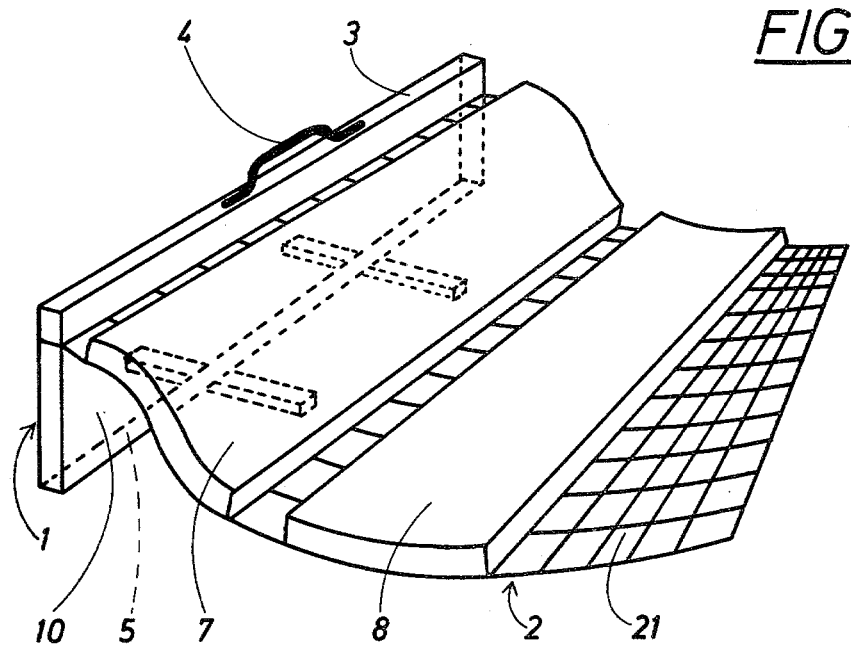

United States Patent [19]

Sandegard

[11] 4,276,875
[45] Jul. 7, 1981

[54] SPLINT FOR EXTREMITIES

[76] Inventor: Jan Sandegard, S-830 43 As, Prästgarden, Sweden

[21] Appl. No.: 27,094

[22] Filed: Apr. 4, 1979

[51] Int. Cl.³ .............................................. A61F 5/04
[52] U.S. Cl. .................................... 128/89 R; 128/94
[58] Field of Search ..................... 128/87 C, 88, 89 R, 128/94, 84 C

[56] References Cited

U.S. PATENT DOCUMENTS

| | | | |
|---|---|---|---|
| 821,619 | 5/1906 | Drier | 128/88 |
| 1,383,928 | 7/1921 | Gassette | 128/88 |
| 1,418,486 | 6/1922 | Smith | 128/88 |
| 2,138,975 | 12/1938 | Malik | 128/88 |
| 2,868,193 | 1/1959 | Kreft | 128/89 R |
| 3,653,378 | 4/1972 | Reuther | 128/88 |
| 4,019,504 | 4/1977 | Sterling | 128/88 |

Primary Examiner—Kyle L. Howell
Assistant Examiner—C. W. Shedd

[57] ABSTRACT

The present invention relates to a splint for extremities and comprising a substantially stiff elongated frame and at least one supporting means, which can be connected to the frame and provided for the supporting and fixation of the extremity. According to the invention the objects of the same are obtained by means of a splint in which the supporting means comprises at least one flexible web provided to form a wrapping element for the extremity, which web exhibits a first edge fastened to the frame along an extension in the longitudinal direction of the same and thereby in the longitudinal direction of the extremity in its intended position, and a second edge, which is opposed to the first mentioned edge and arranged to be attached to the frame by means of a fastening means, which substantially extends parallel to said extension along which the first edge of the web is fastened, so that the web in a first position can form a spread-out surface, when the other edge is free, and a bag-shaped wrapping element for the extremity, when the other edge is attached to the fastening means.

10 Claims, 11 Drawing Figures

SPLINT FOR EXTREMITIES

The present invention relates to a splint for extremities and comprising a substantially stiff elongated frame and at least one supporting means, which can be connected to the frame and provided for the supporting and fixation of the extremity.

In connection with fractures and also certain other types of injuries of the extremities an immobilization is required by splinting the extremity as soon as possible after the injury has occured. There are different variants of devices known for this purpose, which are intended for temporary use, i.e. until the injured subject has come under treatment in a hospital, and it is for example earlier known to use splints, which by means of bands, rollers, straps or similar are attached to the injured extremity and are applied in such a manner against the injured extremity that the contact surface of the same is very limited. For a fully satisfactory fixation it is therefore necessary that the padding is applied between the splint and the extremity. When applying bands or straps, it is often necessary that the extremity is lifted several times with concomitant pain for the patient.

It is further known to use inflatable cushions of plastic foil, which are given stability by gas injection. Such cushions have a manifest drawback due to the fact that too high a pressure can ensue around the injured extremity, which results in lack of nourishment in the injured tissue as a consequence of a squeeze of the capillary vessels, where the exchange of nutritive substances between the blood and the tissue takes place. On the other hand if the pressure in the plastic cushions is less than the pressure in the capillary vessels, 20-25 mm Hg, the stability will be insufficient for the fixation of by way of example a fractured leg.

There is further a known type of splint cushion comprising a sack, in which a great many plastic pellets are enclosed. This device gives stability by an underpressure being produced in the sack, so that its plastic pallets are locked in the form the arrangement has acquired round the injured extremity. If the swelling in the injured region increases, while the cushion is applied, it results in an adverse increase of the pressure in this region.

The function of both these devices implies that the cushions and the sacks respectively are tight, which is difficult to guarantee, when they are used after a long time of storage under unprotected climatic conditions. There is also a risk that the cushion will be punctured at the very site of an accident, where glass splinter, sharp-pointed stones or other pointed objects can occur. Accessories in the form of vacuum pumps are required for the vacuum type cushion, which results in a considerably higher cost for this appliance as compared with other splints.

It is an object of the present invention to provide a splint, which does not exhibit the drawbacks of the known solutions, but satisfies very great medical demands at a comparatively reasonable cost.

According to the invention the objects of the same are obtained by means of a splint in which the supporting means comprises at least one flexible web provided to form a wrapping element for the extremity, which web exhibits a first edge, fastened to the frame along an extension in the longitudinal direction of the same and thereby in the longitudinal direction of the extremity in its intended position, and a second edge, which is opposed to the first mentioned edge and arranged to be attached to the frame by means of a fastening means, which substantially extends parallel to said extension along which the first edge of the web is fastened, so that the web in a first position can form a spread-out surface when the other edge is free, and a bag-shaped wrapping element for the extremity, when the outer edge is attached to the fastening means.

Figure 2:
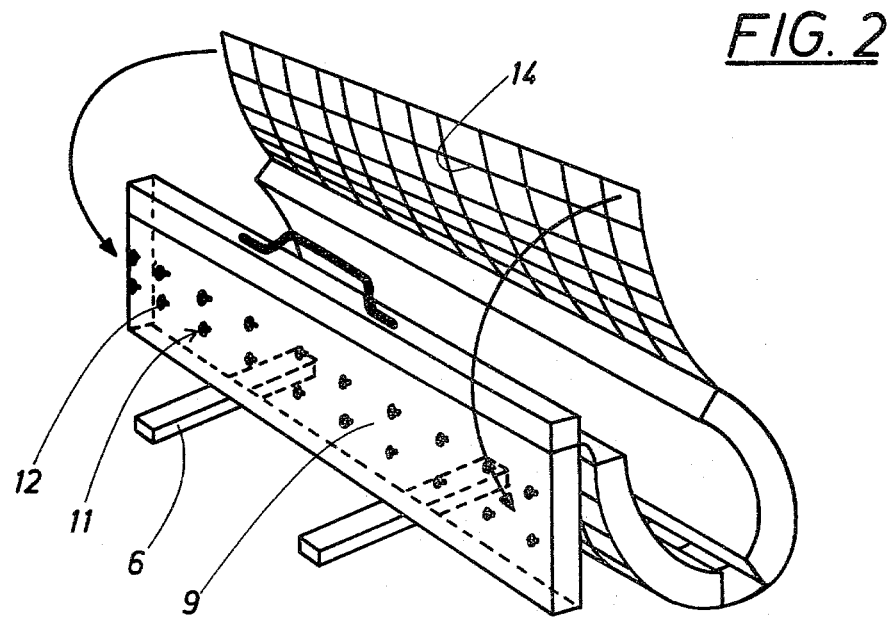
Figure 3:
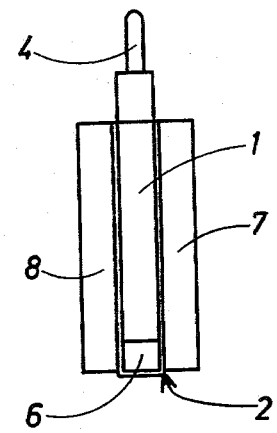
Figure 4:
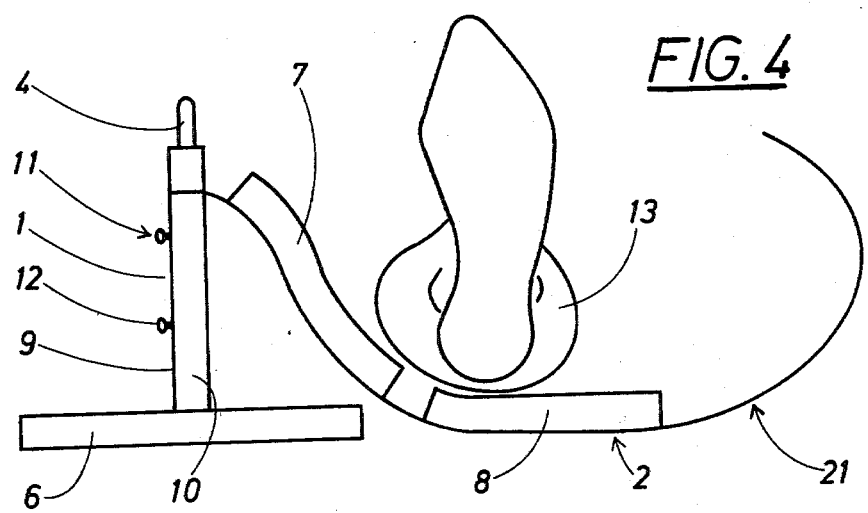
Figure 5:
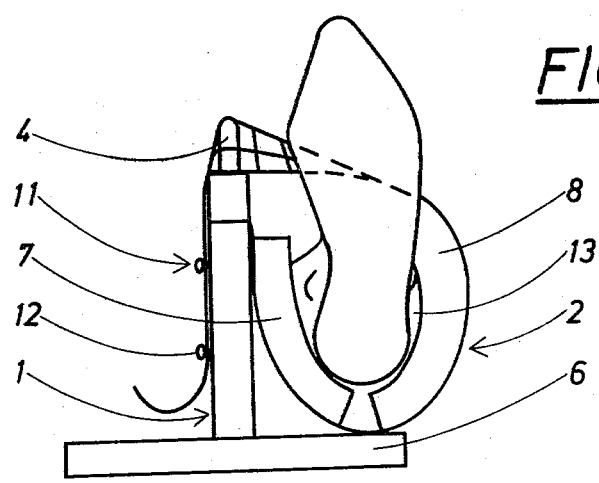
Figure 6:
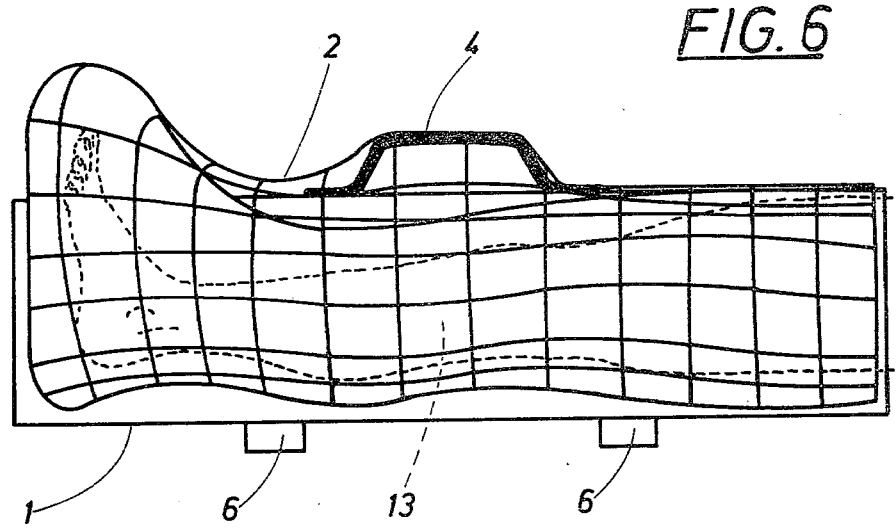
Figure 7:
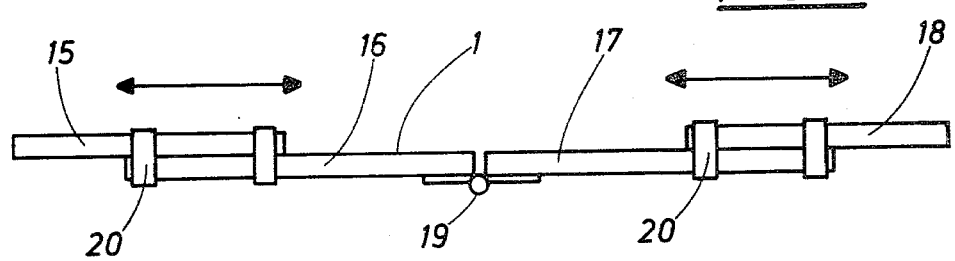
Figure 8:
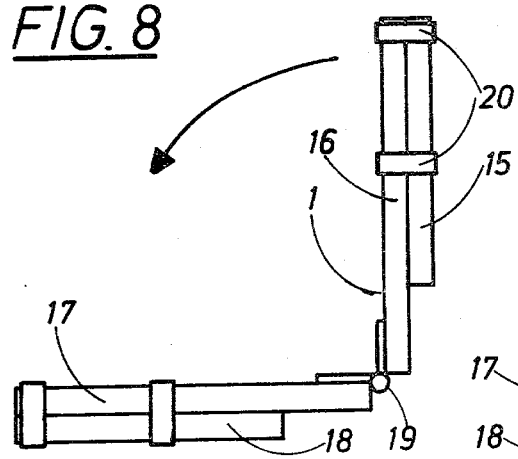
Figure 9:
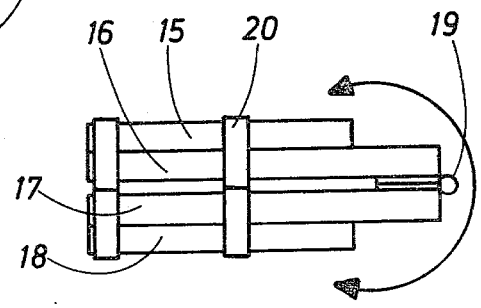
Figure 10:
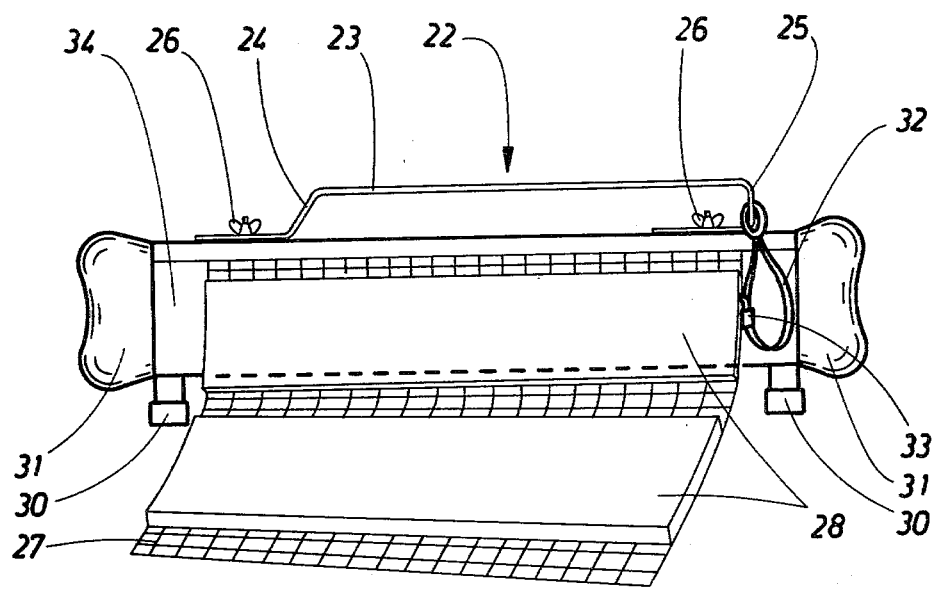
Figure 11:
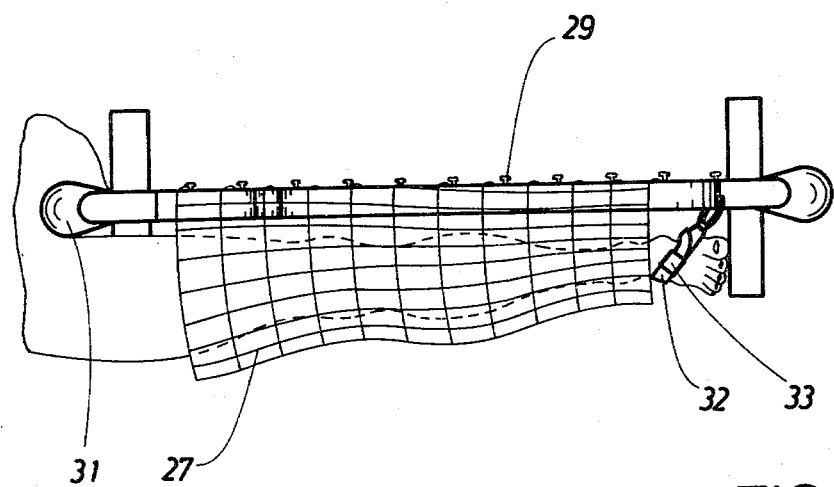

The invention will now be described in the following by means of three examples of embodiment, reference being made to the accompanying drawings, in which FIGS. 1 and 2 are two different perspective views of the splint according to the invention according to a first embodiment, from which the principle of the invention is evident;

FIGS. 3, 4 and 5 exhibit different steps in the handling of the splint according to the present invention as seen in end views;

FIG. 6 is a side elevational view of the splint in a condition, in which it is applied to an extremity;

FIGS. 7, 8 and 9 schematically show a frame of the splint in an embodiment suitable for convenient use;

FIGS. 10, 11 are showing the third embodiment, FIG. 10 being a side elevational view and FIG. 11 a top elevational view.

The splint according to the present invention is the result of a particularly practical arrangement of comparatively simple elements in such a manner that a restful support of the injured extremity is obtained without any unequal distribution of pressure and avoiding local pressure spots that a volume swell is permitted, which is very important when a swelling of the injured extremity occurs, that a correctly adjusted fracture position is maintained, that the extremity can be lifted without anybody having to lift it from its underside, that its handling is extremely simple and time saving, that it can stand storage during a long period of time, that its functional efficiency is not jeopardized in connection with its use on the scenes of accidents with glass splinter or other sharp objects, and that it requires very little space in folded up condition as well as in its condition of use.

According to the embodiment of the splint shown in FIGS. 1 and 2 it is substantially composed of a long frame 1 and a wrapping element 2 connected to the same. The frame 1 is made of a comparatively stiff material, as wood, a stiff non-elastic plastic material, metal or similar. A handle 4 is mounted on top of the upper longitudinal edge portion 3 of the frame. Two pivotable supports 6 which are shown in a swung-out position in FIGS. 1 and 2, i.e. the position of use, are provided at the lower longitudinal edge 5 of the frame. In the illustrated example the wrapping element 2 comprises a net shaped web, which along one edge is permanently fastened to the frame 1. The wrapping element 2 further exhibits a padding consisting of two pads 7, 8 made of a comparatively soft, yielding material, as plastic foam or similar, suitably provided with a surface cover, which is easy to clean, such as a cloth covering or similar. A fastening means 11 in the form of two rows of fastening elements 12 is provided on the one side 9 of the frame 1, facing away from the side 10, to which the wrapping element 2 is permanently fastened, said fastening element 12 being of nail-shaped resemblance and provided with a head, located at a distance from the side 9, and a neck portion extending between the head and said side. The net-shaped web 2 is arranged to be detachably attached to said fastening elements in a manner that will be described below.

The splint according to the invention occupies very little space in folded-up condition, i.e. in the condition for storage and transportation, when it is not used, as is evident from FIG. 3. The supports 6 are then retracted by pivoting round an upright shaft and then extend in the longitudinal direction of the frame 1. The net-shaped web 2 which thus along one of its edges is permanently fastened to the frame 1, is wrapped round the frame 1 in such a manner that the pads 7, 8 bear each one against its side 10, 9 of the frame. As is evident from FIG. 3 the dimensions of the pads 7, 8, at least to some extent, are preferably adapted to the sides 9, 10 of the frame 1 and attached to the net-shaped web 2 in such positions that in the the folded-up condition, they can be positioned substantially right in front of said sides of the frame. As is evident from FIG. 1, the pads 7, 8 are in the present embodiment suitably interspaced, and in folded-up condition the interspace will substantially be located right in front of the lower longitudinal edge 5 of the frame and the retracted supports 6 whereas the pad 7 positioned closest to the permanent attachment of the net-shaped web to the frame likewise exhibits an interspace in relation to said frame, giving a suitable positioning of the pad. The folded-up condition is suitably maintained by the net-shaped web 2 being hooked-up on the fastening elements of the fastening means 11. Preferably, the net-shaped web is made as an unbroken web and thus extends also on the back of the pads 7, 8. The portion 21 of the net-shaped web positioned outside of the outer pad 8 is in a suitable manner folded in inside one of the pads.

The handling of the splint at the use is very simple and can be quickly performed, as is evident from FIGS. 4 and 5. The net-shaped web 2 is folded out and the supports 6 are swung out. While the splint with the supports 6 and a portion of the net-shaped web 2 rests on a foundation, the injured extremity, which in the illustrated example is a leg 13, can be laid on the net-shaped web, whereafter said net-shaped web is wrapped around the leg and with its outer portion 21 is fastened in the fastening element 12 of the fastening means 11 by the meshes 14 of the net-shaped web being hooked up round the neck portions of the fastening elements and retained by means of the heads forming part of said elements. Before the net-shaped web 2 is definitely fastened, it is tightened in such a manner that a sufficient support of the leg is obtained and an equally distributed pressure is obtained above the location of the injury. The pads 7, 8 contribute to the equal distribution of pressure and permit a possible increase in volume because of swelling of the injured region. From FIG. 6 it is evident how well a wrapping in the form of a net-shaped web 2 according to the example shown adapts itself to the shape of the extremity.

After the injured extremity has been supported in the manner shown in FIG. 5, the other leg is placed on top of the supports 6 on the other side of the frame 1, so that this leg, thus, rests upon the supports. Then both the legs can be lifted up simultaneously by means of the handle 4, and it is not necessary to directly support the injured leg, whereby unnecessary pain is avoided. In this arrangement the handling of the splint is also facilitated by the carefully adjusted balance on account of both legs being lifted with the centre of gravity positioned between them.

As is especially evident from FIG. 5 it is an essential condition in the present invention that the injured extremity is connected to the frame by means of the net-shaped web 2, because the special manner in which the same is fastened to the splint permits the extremity to be supported as in a suspending arrangement. Thus the fastening of the net-shaped web 2 is providing a connection of both the ends of the net-shaped web to the frame 1 with both the areas of suspension in relatively close connection to each other, and above the lower part of the extremity, i.e. relatively high up in the frame and in such a manner that the injured extremity is not squeezed between the wrapping element and the frame, which thus is the case with the appliances of the prior art, and which among other things result in the drawback of local pressure spots. Irrespective of the place, where the free end of the net-shaped web is fastened, the place of suspension substantially is the longitudinal edge portion 3 of the frame (and in a certain degree also the handle 4). Thus, this place of suspension is located close to the permanent fastening point of the net-shaped web 2. In the example shown this permanent fastening results in a very stable arrangement due to the fact that the net-shaped web with its fixed end is squeezed-in in a joint or groove of the frame 1.

An example of a practical embodiment of the frame 1 is shown in FIGS. 7, 8, 9. As is evident from FIG. 7, it is deivided up in several units, in the example shown in four parts 15, 16, 17, 18. Both the parts 16 and 17 are in between them articulated by means of hinges 19, whereas the parts 15 and 18 are displaceable in relation to other parts as seen in the longitudinal direction of the frame, as said parts 15 and 18 are coupled to the other parts by means of guiding elements 20, which permit different possibilities of adjustment of the frame to correspond to different longitudinal measures according to the length of the extremity. From FIG. 8 it is evident that by means of the hinge 19 the frame 1 can be set in different angular positions by way of example for the fixation of an arm. As is evident from FIG. 9 the possibility of longitudinal displacement and articulation of the elements permits a folding-up of the frame 1 to very small interior measures, when the appliance is not in use. The guiding elements 20 by way of example comprise C-shaped or ractangular means, which are fixed to one of the two in between them displaceable parts 15, 16 and 17, 18 respectively and permit a displacement of the other element. Some kind of terminal stop is provided for the displaceable elements 15, 18 and, moreover, the displaceability is chosen with a suitably adjusted friction between the in between them displaceable surfaces. The parts 16 and 17 of the frame 1 can alternatively be in between them hinged round a shaft extending in the direction along the paper.

By the in FIGS. 10 and 11 shown embodiment an arrangement making the frame expandable is used to make the spint usable as a traction device for the extremity. In some types of fractures it is desirable that the extremity is subjected to a traction force which is possible by means of the splint of the third embodiment.

According to FIGS. 10, 11 a frame 34 of the splint is provided with an elongated handle 22, comprising a bar 23 and a first end portion 24 and a second end portion 25. The handle 22 is slidable in the longitudinal direction of the frame 21 and can be locked in different positions by means of tightable screws 26 stretching through elongated openings in the respective end portions 24, 25.

As described in connection with the other embodiments, the frame 34 is provided with a wrapping in the form of a net-shaped web 27 with pads 28 and on the frame means 29 for the attachment of the free end of the web 27. Further, the frame 34 is provided with supports 30 and at both ends an upholstery 31. A strap 32 forming a loop is attached to the end portion 25 of the handle 22. The width of the loop can be adjusted by means of a buckle 33 on the strap 32.

In FIG. 11 it is shown how the splint is used for traction treatment. The frame 34 is inserted between the legs of the patient with the upholstery 31 resting in the crutch. The strap 32 is laid around the ancle and tightened so that it cannot be drawn over the foot. Thereafter the leg is stretched by pulling the handle 22 outwards so that the leg will be subjected to a traction force. When a suitable traction force is reached the handle 22 is locked by means of the screw 26, thereafter the leg can be supported on the frame by means of the web 27 in the way described before.

In FIG. 11 it is shown how the right leg is treated by means of the splint. If the leg has to be treated instead, the handle 22 has to be reversed so that the end portion 25 is directed towards the left end of the frame 21 as seen from that side of the frame, from which the web 29 is extending (see FIG. 10). As the strap 32 is attached to the end portion 25 of the handle the foot of the patient has to be placed at said left end of the frame and the upholstery 31 of the opposite end has to be placed in the crutch.

If it is desirable to exercise a resilient traction force against the leg the handle can be provided with a spring or similar. It is also possible to attach the strap 32 to the end portion 25 by means of a spring or similar resilient means. The traction splint can also be adapted for use in arm fractures. Traction treatment is, however, not so common by fractures of this kind. If an arm has to be treated the upholstery has to be positioned in the armpit and the strap has to be laid around the wrist.

The invention is not limited to the example of embodiment described above and illustrated in the drawings, but can be varied within the scope of the claims. By way of example the net-shaped web serving the purpose of a wrapping element can be substituted by another wrapping element for example a material of cloth, which possibly is somewhat resilient. The fastening means can moreover be of another design and for example be substituted by Velcro tape of bands adjustable by means of buckles. The pads can be of another size or design or possibly by completly omitted. The supporting legs can be of metal and thereby exhibit thinner dimensions, and they can also be hinged in a different manner, so that they for example are lowered towards the sides of the frame. It can in principle also be imagined that the splint can be modified for use for two injured extremities, as legs, with the fastening of the free end of the web positioned at the upper edge portion of the frame and with the net-shaped web 2 of greater length, which is sufficient for both legs, or else the net-shaped web can be divided up in two symmetrically fastened portions.

I claim:

1. A medical splint for application to at least one injured extremity for the support and fixation of the latter, comprising: a substantially rigid, elongated frame having upper and lower longitudinal edge portions, and a wrapping element having four pairwise opposite edge portions, a first of said edge portions being connected to said frame and extending substantially parallel to and adjacent said upper edge portion, a second edge portion opposite said first edge portion being adapted to be applied to said upper longitudinal edge portion and releasably attached to said frame, fastening means at said frame for attaching said second edge portion to said frame, said wrapping element being selectively movable from a first position to a second position, and vice versa, in said first position said wrapping element forming a spread-out surface with said second edge portion in unattached condition, on which surface the extremity may be placed, in said second position said wrapping element being wrapped around the extremity and forming a sling hanging down from said upper edge portion, with the frame positioned outside the sling.

2. A splint according to claim 1, wherein said frame is provided with supporting means with a downwards facing supporting surface adapted to be placed on a foundation and wherein the distance between said upper edge portion and said supporting surface exceeds the height of the sling, so that the extremity will be in a suspended position above the foundation.

3. A splint according to claim 2, wherein the frame has an upright lateral side arranged to constitute a resting surface for the extremity in the sling-like wrapping element in the attached position of the second edge portion.

4. A splint according to claim 3, wherein the attachment of the sling-like wrapping element by said fastening means with respect to the length of the sling between said first edge portion and the upper edge portion of the frame is adjustable.

5. A splint according to claim 4, wherein said wrapping element is a net.

6. A splint according to claim 5, wherein said fastening means comprise at least one row of pins to which meshes of said net may be hooked.

7. A splint according to claim 5, wherein said net is provided with at least one pad for contact with the extremity.

8. A medical splint for application to at least one injured extremity for the support and fixation of the latter, comprising: a substantially rigid, elongated frame having upper and lower longitudinal edge portions, and a wrapping element having four pairwise opposite edge portions, a first of said edge portions being connected to said frame and extending substantially parallel to and adjacent said upper edge portion, a second edge portion opposite said first edge portion being adapted to be applied to said upper longitudinal edge portion and releasably attached to said frame, fastening means at said frame for attaching said second edge portion to said frame, said wrapping element being selectively movable from a first position to a second position, and vice versa, in said first position said wrapping element forming a spread-out surface with said second edge portion in unattached condition, on which surface the extremity may be placed, in said second position said wrapping element being wrapped around the extremity and forming a sling hanging down from said upper edge portion, with the frame positioned outside the sling, said frame being generally rectangular, and a subframe juxtaposed to and connected to said frame at one of the narrow ends of said rectangular frame, whereby said frame can be lengthened.

9. Splint according to claim 8, wherein the subframe is slidable relative to the frame and wherein one of said narrow ends is provided with a support for the support of the frame against a supporting portion of a patient, said subframe having holding means to be attached to an outer end of the extremity so that after extension of the splint and attachment of said end of the extremity to said holding means, the extremity can be subjected to traction.

10. Splint according to claim 9, wherein both ends of the frame are provided with supports and with holding means so that the splint may be rotated end over end.

* * * * *

UNITED STATES PATENT AND TRADEMARK OFFICE
CERTIFICATE OF CORRECTION

PATENT NO. : 4,276,875
DATED : July 7, 1981
INVENTOR(S) : JAN SANDEGARD

It is certified that error appears in the above-identified patent and that said Letters Patent are hereby corrected as shown below:

[30] Foreign Application Priority Data

Apr. 6, 1978 [SE] Sweden. . . . . 7803876

Signed and Sealed this

Twenty-second Day of September 1981

[SEAL]

Attest:

GERALD J. MOSSINGHOFF

Attesting Officer            Commissioner of Patents and Trademarks